United States Patent [19]

Harandi et al.

[11] Patent Number: 4,826,507
[45] Date of Patent: May 2, 1989

[54] INTEGRATED ETHERIFICATION AND OXYGENATES TO GASOLINE PROCESS

[75] Inventors: Mohsen N. Harandi, Lawrenceville; Hartley Owen, Belle Mead, both of N.J.

[73] Assignee: Mobil Oil Corporation, New York, N.Y.

[21] Appl. No.: 130,261

[22] Filed: Dec. 8, 1987

[51] Int. Cl.[4] .......................... C10L 1/18; C07C 41/06
[52] U.S. Cl. ........................................ 44/77; 568/697; 568/699
[58] Field of Search .................... 568/697, 699; 44/77; 585/331, 333, 415

[56] References Cited

U.S. PATENT DOCUMENTS

| 3,931,349 | 1/1976 | Kuo . | |
|---|---|---|---|
| 3,960,978 | 6/1976 | Givens | 585/533 X |
| 4,021,502 | 5/1977 | Plank | 585/533 X |
| 4,404,414 | 9/1983 | Penick et al. . | |
| 4,456,779 | 6/1984 | Owen et al. . | |
| 4,511,747 | 4/1985 | Wright | 585/533 X |
| 4,542,252 | 9/1985 | Graziani et al. . | |
| 4,544,776 | 10/1985 | Osterburg | 568/697 |
| 4,603,225 | 7/1986 | Colaianne | 568/697 |
| 4,684,757 | 8/1987 | Avidan et al. . | |

FOREIGN PATENT DOCUMENTS

| 0075838 | 4/1983 | European Pat. Off. | 568/697 |
| 0206594 | 12/1986 | European Pat. Off. | 568/697 |
| 2705538 | 8/1978 | Fed. Rep. of Germany | 568/699 |

Primary Examiner—William R. Dixon, Jr.
Assistant Examiner—James M. Hunter, Jr.
Attorney, Agent, or Firm—Alexander J. McKillop; Charles J. Speciale; L. G. Wise

[57] ABSTRACT

An integrated once through process for the production of ether-rich liquid fuels containing MTBE and TAME by etherifying a hydrocarbon feedstock containing $C_{4+}$ isoalkenes in the presence of a high stoichiometric excess of lower alkyl alcohol. Unreacted alcohol and olefins are passes to a zeolite catalyzed conversion reactor under olefinic and oxygenates conversion condition whereby gasoline and light hydrocarbons are produced.

14 Claims, 2 Drawing Sheets

INTEGRATED ETHERIFICATION AND OXYGENATES TO GASOLINE PROCESS

BACKGROUND OF THE INVENTION

This invention relates to processes for converting methanol and olefinic hydrocarbons to high octane liquid fuel. In particular, this invention relates to an integrated once through system for the production of methyl tertiary alkyl ethers in the presence of a high excess of methanol combined with the conversion of oxygenates and olefins to gasoline.

In recent years, a major technical challenge presented to the petroleum refining industry has been the requirement to establish alternate processes for manufacturing high octane gasoline in view of the regulated requirement to eliminate lead additives as octane enhancers as well as the development of more efficient, higher compression ratio gasoline engines requiring higher octane fuel. To meet these requirements the industry has developed non-lead octane boosters and has reformulated high octane gasoline to incorporate an increased fraction of aromatics. While these and other approaches will fully meet the technical requirements of regulations requiring elimination of gasoline lead additives and allow the industry to meet the burgeoning market demand for high octane gasoline, the economic impact on the cost of gasoline is significant. Accordingly, workers in the field have intensified their effort to discover new processes to manufacture the gasoline products required by the market place. One important focus of that research is a new process to produce high octane gasolines blended with lower aliphatic alkyl ethers as octane boosters and supplementary fuels. $C_5$–$C_7$ methyl alkyl ethers, especially methyl tertiary butyl ether (MTBE) and tertiary amyl methyl ether (TAME) have been found particularly useful for enhancing gasoline octane. Therefore, improvements to the processes related to the production of these ethers are matters of high importance and substantial challenge to research workers in the petroleum refining arts.

It is known that isobutylene may be reacted with methanol over an acidic catalyst to provide methyl tertiary butyl ether (MTBE) and isoamylenes may be reacted with methanol over an acidic catalyst to produce tertiaryamyl methyl ether (TAME). In these etherification processes, a problem of major importance is the separation of methanol from the etherification reaction product due to the proclivity of methanol to form a very dilute azeotropic mixture with hydrocarbons and the strong solubility of methanol in both water and hydrocarbons. While it would be useful from an equilibrium standpoint to use large excesses of methanol in etherification, subsequent separation problems have limited that process improvement. Due largely to these factors, the cost associated with methanol separation and recycling in the etherification reaction represents approximately 30% of the cost of the total etherification process.

In U.S. Pat. No. 4,684,757 to Avidan et al., the well-known ability of zeolite type catalyst to convert methanol to olefins is utilized by directing unreacted methanol from an etherification reaction to a zeolite catalyzed conversion reaction for conversion to olefin, thereby obviating the need to separate and recycle methanol in the etherification reaction. However, the process of Avidan et al. converts oxygenate feedstock. The process incorporates an alkylation step in one embodiment to produce alkylate as well as $C_5+$ gasoline and $C_5+$ ethers.

The process for the conversion of methanol to olefins utilized in the Avidan et al. patent is but one in a series of analogous processes based upon the catalytic capabilities of zeolites. It is known that zeolites, such as ZSM-5, can convert methanol to hydrocarbons of higher average molecular weight. Depending on various conditions of space velocity, temperature and pressure methanol, and lower oxygenates in general, can be converted in the presence of zeolite type catalyst to olefins which may then oligomerize to provide gasoline or distillate or be converted further to produce aromatics.

The feasibility and adaptability of the basic chemistry of zeolite oxygenates conversion to produce useful conversion processes has been the subject of much inventive research activity. Recent developments in zeolite catalyst and hydrocarbon conversion processes have created interest in using oxygenates and olefinic feedstocks for producing $C_5+$ gasoline, diesel fuel, etc. In addition to the basic work derived from ZSM-5 type zeolite catalyst, a number of discoveries have contributed to the development of a new industrial process. This process has significance as a safe, environmentally acceptable technique for utilizing feedstocks that contain lower olefins, especially $C_2$–$C_5$ alkenes. In U.S. Pat. Nos. 3,960,978 and 4,021,502, Plank, Rosinski and Givens disclose converse of $C_2$–$C_5$ olefins, alone or in admixture with paraffinic components into higher hydrocarbons over crystalline zeolites having controlled acidity. Garwood et al. have also contributed improved processing techniques in U.S. Pat. Nos. 4,150,062, 4,211,640 and 4,227,992. The above identified disclosures are incorporated herein by reference.

A well-known process for the conversion of oxygenates to gasoline is the methanol to gasoline process, known as MTG. The process is described in U.S. Pat. No. 3,931,349 to Kuo, U.S. Pat. No. 4,404,414 to Penick et al. and in the publication by C. D. Chang, Catal. Rev.-Sci. Eng., 25, 1 (1983). These references are incorporated herein in their entirety.

Recognizing the limiting problems of the etherification processes to produce MTBE and TAME and the potential that resides in the general area of the chemistry of oxygenate and olefin conversion with zeolites to resolve those problems, the following objectives of the instant invention have been established:

first, it is an object of the present invention to provide a once through integrated process for the production of liquid fuel mixtures from olefin containing feedstock and a high excess of lower alkyl alcohols by etherification and oxygenate and olefin conversion reactions.

It is another object of the present invention to provide a once through process for the production of liquid fuels of enhanced octane value containing MTBE and TAME.

A further object of the instant invention is an integrated liquid fuels process wherein the etherification reaction is conducted without the need to recycle excess alcohol to the etherification reaction.

A further object of the present invention is to provide a once through liquid hydrocarbon integrated process incorporating etherification with oxygenates and olefin conversion wherein valuable isoalkenes in the hydrocarbon feedstream are etherified prior to the conversion reaction.

SUMMARY OF THE INVENTION

According to the present invention, a novel integrated process has been discovered whereby the etherification of isoalkenes can be conducted using lower alcohols such as methanol. In particular, the etherification reaction can be conducted using large excesses of the alcohol reactant. Excess alcohol in the etherification effluent stream is not recycled to the etherification reaction as is commonly practiced but is passed for concurrent conversion with a portion of the effluent hydrocarbon stream to a conversion reactor where in the presence of zeolite-type catalyst the alcohol and olefins present in the etherification reaction effluent stream are converted to gasoline. Fresh alcohol is the feed to the etherification reaction, i.e., alcohol unadulterated with alcohol recycled or recovered from the integrated etherification conversion process.

It has been discovered that, in addition to the advantage of obviating the need to separate and recycle methanol in the etherification reaction, substantial benefits accrue in the present invention to the MTG process and olefins to gasoline conversion. Inert gasiform components in the etherification effluent stream, when combined with inert components in the olefinic hydrocarbon feedstream to the conversion reactor, serve to dilute the exothermic reaction therein reducing the need to recycle inert diluents as typically practiced. To that extent the MTG process is advantageously simplified.

It has been discovered that the integrated process described herein can be conducted in a once through configuration using fresh methanol without providing a recycle stream from the zeolite catalyzed conversion step to the etherification step. The design makes the MTG process more attractive for refinery applications since the methanol feed handling facility is in common with the etherification reaction, and the zeolite conversion reactor and recovery sections for the conversion of methanol to gasoline are in common with the conversion of olefins to gasoline.

The present invention describes an integrated once through process for the production of ether-rich liquid fuels, comprising; reacting a mixture of excess lower alkyl alcohol and a hydrocarbon feedstock containing $C_4+$ isoalkenes in the presence of acid etherification catalyst under etherification conditions whereby lower alkyl tertiary alkyl ethers are produced; separating the etherification effluent stream to provide a first stream comprising ether-rich gasoline and a second stream comprising unreacted lower alkyl alcohol and olefinic hydrocarbons; contacting said second stream with an acidic metallosilicate catalyst under olefinic and oxygenates conversion conditions at elevated temperature whereby $C_6+$ gasoline is produced. In the process, the second stream after etherification can be mixed with an auxiliary or additional feedstock comprising olefinic light gas, such as fuel gas, before contacting with the acid metallosilicate cataylst for conversion to gasoline.

The high excess of lower alkyl alcohol in the esterification reaction represents a high stoichiometric excess of the alcohol reactant over $C_4+$ isoalkenes whereby the etherification reaction equilibrium is shifted to the formation of $C_5+$ ethers.

More particularly, the invention describes an integrated continuous process for producing tertiary alkyl ethers and gasoline range hydrocarbons comprising the steps of:

(a) contacting a first liquid reaction mixture in a single pass with an acid etherification catalyst under etherification conditions, said first reaction mixture comprising $C_4$-$C_9$ hydrocarbons containing $C_4$-$C_7$ isoalkene components and $C_6+$ gasoline range non-etherifiable aliphatic components, and a lower aliphatic alcohol reactant, said alcohol being present in more than 30% stoichiometric excess of the isoalkene component;

(b) recovering an etherification reaction effluent containing $C_5+$ tertiary alkyl ether, gasoline range hydrocarbons, unreacted alcohol and light olefinic hydrocarbons;

(c) distilling the etherification reaction effluent to provide a first product stream comprising a liquid mixture of $C_5+$ ether and gasoline range hydrocarbons, and a second volatile low molecular weight reaction mixture comprising unreacted alcohol and light olefinic hydrocarbons; and (d) contacting the second reaction mixture with an acid medium pore metallosilicate zeolite catalyst at elevated temperature to convert the alcohol and light olefinic hydrocarbons to a second product stream having average molecular weight greater than the second reaction mixture.

DETAILED DESCRIPTION OF THE INVENTION

Figure 1:
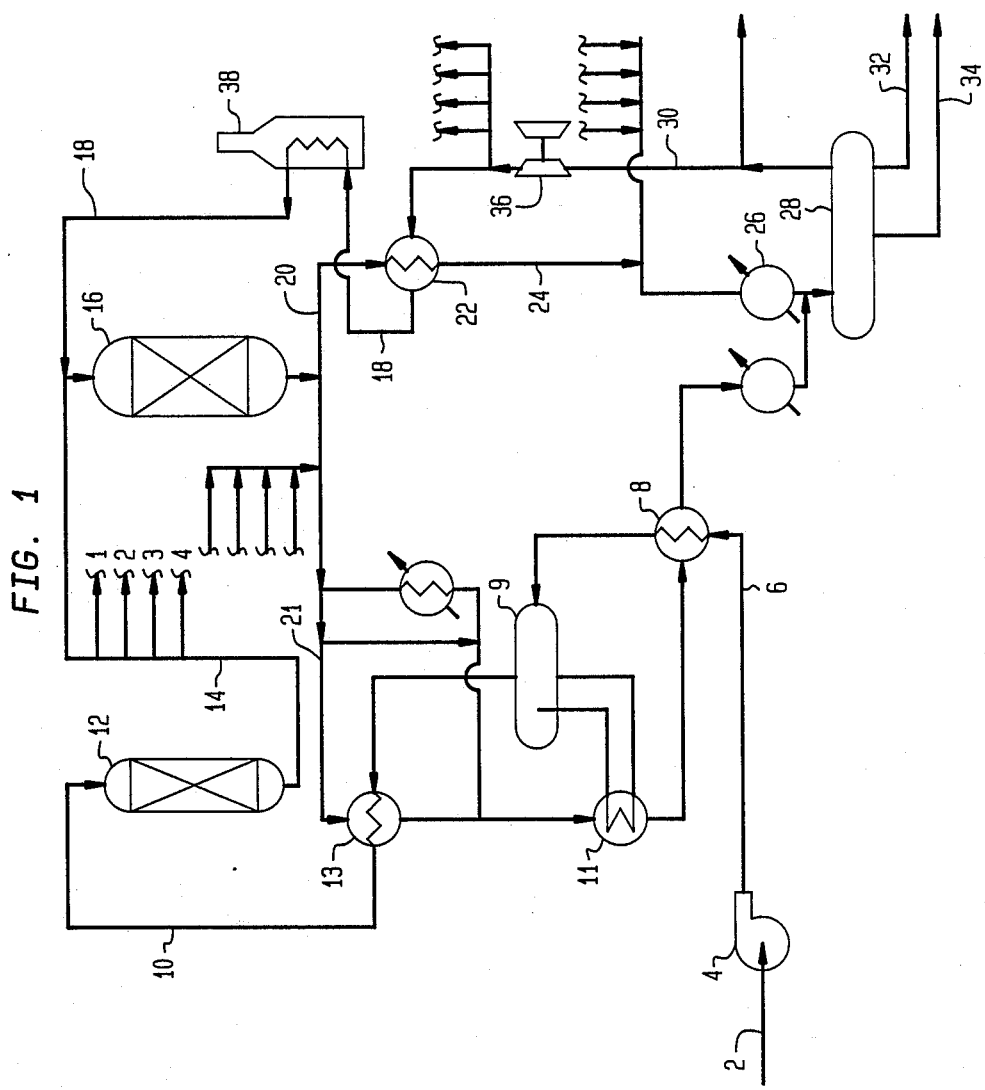
FIG. 1 is a flow diagram of the MTG process for the conversion of methanol to gasoline.

In the preferred embodiments of this invention, methanol is reacted with the hydrocarbon feedstock such as FCC light naptha containing olefins, particularly iso-olefins, to produce methyl tertiary alkyl ethers and gasoline range hydrocarbons. In the reaction, methanol is generally present in an excess amount between 10 percent to 100 percent, based upon iso-olefins. Following etherification, excess methanol and olefins are passed for concurrent conversion to a conversion reactor containing zeolite type catalysts, such as ZSM-5, to produce gasoline, LPG and lighter products.

Methanol may be readily obtained from coal by gasification to synthesis gas and conversion of the synthesis gas to methanol by well-established industrial processes. As an alternative, the methanol may be obtained from natural gas by other conventional processes, such as stream reforming or partial oxidation to make the intermediate syngas. Crude methanol from such processes usually contains a significant amount of water, usually in the range of 4 to 20 wt%. The etherification catalyst employed is preferably an ion exchange resin in the hydrogen form; however, any suitable acidic catalyst may be employed. Varying degrees of success are obtained with acidic solid catalysts; such as, sulfonic acid resins, phosphoric acid modified kieselguhr, silica alumina and acid zeolites. Typical hydrocarbon feedstock materials for etherification reactions include olefinic streams, such as FCC light naphtha and butenes rich in iso-olefins. These aliphatic streams are produced in petroleum refineries by catalytic cracking of gas oil or the like.

The reaction of methanol with isobutylene and isoamylenes at moderate conditions with a resin catalyst is known technology, as provided by R. W. Reynolds, et al., *The Oil and Gas Journal,* June 16, 1975, and S. Pecci and T. Floris, *Hydrocarbon Processing,* December 1977. An article entitled "MTBE and TAME—A Good Octane Boosting Combo," by J. D. Chase, et al.,

*The Oil and Gas Journal,* Apr. 9, 1979, pages 149-152, discusses the technology. A preferred catalyst is a bifunctional ion exchange resin which etherifies and isomerizes the reactant streams. A typical acid catalyst is Amberlyst 15 sulfonic acid resin.

MTBE and TAME are known to be high octane ethers. The article by J. D. Chase, et al., *Oil and Gas Journal,* Apr. 9, 1979, discusses the advantages one can achieve by using these materials to enhance gasoline octane. The octane blending number of MTBE when 10% is added to a base fuel (R+O=91) is about 120. For a fuel with a low motor rating (M+O=83) octane, the blending value of MTBE at the 10% level is about 103. On the other hand, for an (R+O) of 95 octane fuel, the blending value of 10% MTBE is about 114.

Processes for producing and recovering MTBE and other methyl tertiary alkyl ethers from $C_4$-$C_7$ iso-olefins are known to those skilled in the art, such as disclosed in U.S. Pat. Nos. 4,544,776 (Osterburg, et al.) and 4,603,225 (Colaianne et al.). In the prior art various suitable extraction and distillation techniques are known for receiving ether and hydrocarbon streams from etherification effluent.

In the integrated process of the present invention, zeolite type catalyst converts alcohol, such as excess etherification methanol, and olefins to gasoline and other liquid products. It is well-known that the conversion of methanol to gasoline proceeds through the formation of ethers and olefins which, in turn, oligomerize to higher hydrocarbon gasoline and distillate products. In the process for catalytic conversion of olefins to heavier hydrocarbons by oligomerization using acid crystalline zeolite, such as ZSM-5 type catalyst, process conditions can be varied to favor the formation of either gasoline or distillate range products. In the present invention, the feed to the conversion reactor is preferably a combined feed of methanol and olefins. Operating details for the typical conversion of olefins to gasoline or distillate are disclosed in U.S. Pat. Nos. 4,456,779; 4,497,968 to Owen et al. and 4,433,185 to Tabak, which are incorporated herein by reference.

A conventional methanol to gasoline (MTG) plant design may be readily adapted to process the combined methanol or methanol and olefins feed of the instant invention.

Referring now to FIG. 1, a typical process flow diagram of the MTG process is presented. Crude methanol in a liquid phase condition is charged to the process by conduit 2 communicating with pump 4. The methanol is compressed to about 1120 kPa (160 psig) in pump 4 and then passed by conduit 6 to heat exchanger 8 wherein the temperature of the liquid methanol is raised to about 204° C. (400° F.). The thus preheated methanol is vaporized in indirect heat exchanger 8 before it is passed by conduit 10 to the inlet of the dimethyl ether forming catalytic reactor 12. In catalyst containing reactor 12, a fixed bed of gamma alumina catalyst is maintained as a fixed bed of catalyst through which the methanol reactant passed downwardly through or as an annular bed of catalyst for radial flow of reactant material therethrough. A single downflow fixed catalyst bed or a plurality of separate fixed downflow catalyst bed are arranged for converting the methanol feed under restricted temperature conditions as herein described to essentially an equilibrium product comprising methanol, dimethyl ether or water existing at a temperature of about 315° C. (600° F.) due to the exothermic temperature rise catalytically generated in the operation. The equilibrium product thus obtained may be construed as an ether rich product which is then passed by conduit 14 to a second reactor stage 16 housing one or more separate and sequentially arranged beds of a ZSM-5 type of crystalline zeolite. For the purpose of this specific discussion, the crystalline zeolite employed in the second reactor stage is a HZSM-5 crystalline zeolite.

In the combination operation herein described, it is preferred to employ a low pressure drop catalyst system in reactor 16. A diluent material introduced by conduit 18 is combined with the ether rich effluent obtained as hereinbefore discussed before contact of the mixture is made with the HZSM-5 crystalline zeolite catalyst under heat generating or exothermic reaction conditions controlled to restrict the temperature increase between the reactor inlet and reactor outlet not to exceed about 93° C. (200° F.) and preferably not to exceed about 149° C. (300° F.). The conversion of the ether rich effluent by the HZSM-5 catalyst is highly exothermic as discussed above and controlled within desired limits by use of gasiform heat dissipating diluent material. During this highly exothermic operation the ether rich effluent or equilibrium mixture comprising dimethyl ether, methanol and water is controlled to effect the conversion thereof to gasoline boiling range components comprising aromatic and isoparaffins. The aromatic components comprising benzene, toluene and xylene are preferred components over the higher boiling durene aromatic material and every effort is made through temperature restraint, reactant partial pressure, space velocity and reactant plug flow operation to promote this end.

The product effluent of the HZSM-5 reaction zone 16 is passed through one or more cooling steps to reduce the temperature to a desired low temperature. In the specific arrangement of the figure, the effluent is passed by conduit 20 to heat exchanger 22 wherein the effluent temperature is reduced to about 243° C. (470° F.) by indirect heat exchange with diluent material removed therefrom by conduit 18. The diluent will be at a temperature of about 315° C. (600° F.). The partially cooled effluent is removed from heat exchanger 22 and passed by conduit 24 to heat exchanger 26 wherein a further cooling of the effluent to about 227° C. (440° F.) is accomplished.

A portion of reactor 16 effluent is passed through conduit 21 through heat exchangers 8, 11 and 13 to preheat methanol. The effluent is combined in separator 28 after temperature reduction from about 427° C. (800° F.) to 38° C. (100° F.). Recycled gas is separated by conduit and product gasoline is separated by conduit 32 and waste water by conduit 34. Recycle gas, after compression in compressors 36 is returned to the reactor as diluent after heating in heater 38. Diluent temperature is raised from about 38° C. (100° F.) to about 315° C. (600° F.), although recycle gas can be between 293° C. (560° F.) and 399° C. (750° F.), but preferably about 310° C. to 371° C. (590° to 700° F.). Inlet temperatures to the first reactor are normally about 299° C. (570° F.) to 399° C. (750° F.) but preferably about 329° C. (625° F.) to 371° C. (700° F.), although in certain processes temperatures as low as 277° C. (530° F.) may be desirable.

The conversion of methanol, or methanol equivalents, and olefins in the present invention is preferably catalyzed by a crystalline zeolite catalyst having acidic functionality. The preferred class of catalysts is characterized by a Constraint Index of 1 to 12 and a silica:alumina ratio of at least 12:1 and preferably higher e.g. 30:1, 70:1, 500:1, 1600:1 or even higher. As described in U.S. Pat. No. 3,998,889, the Constraint Index of a zeolite is a convenient measure of the extent to which a zeolite provides constrained access to its internal structure for molecules of different sizes. It is therefore a characteristic of the structure of the zeolite but is measured by a test which relies upon the possession of cracking activity by the zeolite. The sample of zeolite selected for determination of the Constrain Index of a zeolite should therefore represent the structure of the zeolite (manifested by its X-ray diffraction pattern) and have adequate cracking activity for the Index to be determined. If the cracking activity of the selected zeolite is too low, the Constraint Index may be determined by using a zeolite sample of the same structure but higher cracking activity which may be obtained, for example, by using an aluminosilicate zeolite of higher aluminum content. Details of the method of determining Constraint Index and of the values of the Index for typical zeolites are given in U.S. Pat. No. 3,998,899 to which reference is made for such details and other information in this respect.

The silica-alumina ratios referred to in this specification are the structural or framework ratios, that is, the ratio for the $SiO_4$ to the $AlO_4$ tetrahedra which together constitute the structure of which the zeolite is composed. This ratio may vary from the silica:alumina ratio determined by various physical and chemical methods. For example, a gross chemical analysis may include aluminum which is present in the form of cations associated with the acidic sites on the zeolite, thereby giving a low silica:alumina ratio. Similarly, if the ratio is determined by thermogravimetric analysis (TGA) of ammonia desorption, a low ammonia titration may be obtained if cationic aluminum prevents exchange of the ammonium ions onto the acidic sites. These disparities are particularly troublesome when certain treatments such as dealuminization methods which result in the presence of ionic aluminum free of the zeolite structure are employed to make highly siliceous zeolites. Due care should therefore be taken to ensure that the framework silica:alumina ratio is correctly determined.

Preferred zeolites which have the specified values of Constraint Index and silica:alumina ratio include zeolites ZSM-5, ZSM-11, ZSM-12, ZSM-35 and ZSM-48, which are described in U.S. Pat. Nos. 3,702,886 (ZSM-5), 3,709,979 (ZSM-11), 3,832,449 (ZSM-12), 4,076,842 (ZSM-23) and 4,016,245 (ZSM-35) and Euroopean Patent Publication No. 15132, and reference is made to these patents for details of these zeolites, their preparation and properties. Of these zeolites, ZSM-5 is preferred.

The zeolite catalyst used is at least partly in the hydrogen form e.g. HZSM-5 but other cations e.g. rare earth cations may also be present. When the zeolites are prepared in the presence of organic cations, they may be quite inactive possibly because the intracrystalline free space is occupied by the organic cations from the forming solution. The zeolite may be activated by heating in an inert atmosphere to remove the organic cations e.g. by heating at over 500° C. for 1 hour or more. The hydrogen form can then be obtained by base exchange with ammonium salts followed by calcination e.g. at 500° C. in air. Other cations e.g. metal cations can be introduced by conventional base exchange techniques.

Figure 2:
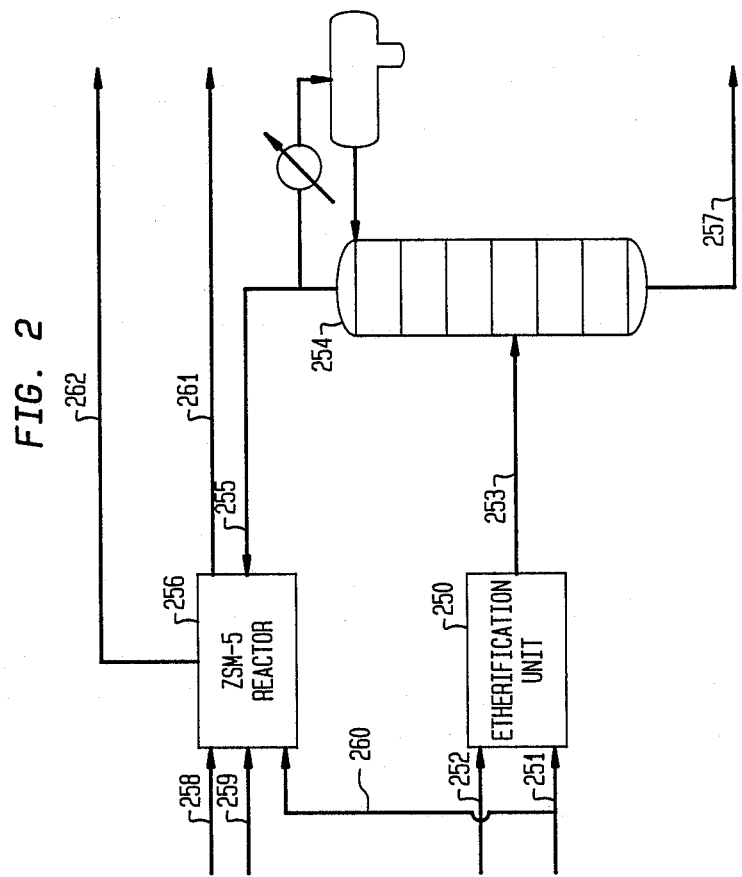
FIG. 2 is a schematic drawing of the process flow diagram of the instant invention.

Referring now to FIG. 2, the once through integrated process of the present invention is illustrated in a flow schematic. Methanol and hydrocarbon reactants are passed to the etherification reactor 250 in conduits 251 and 252. Preferably the hydrocarbon feed is rich in isoalkenes and also contains other paraffinic and olefinic hydrocarbons. By virtue of the discovery embodied in the instant invention, the quantity of methanol passed to the etherification unit is between 10 and 100 percent in excess of the stoichiometric amount needed to react with isoalkenes in an etherification reaction. Etherification is conducted as described heretofore and the etherification product is passed 253 as an effluent stream to separator 254. Methanol is separated overhead as an azeotropic mixture with $C_4$-paraffinic and olefinic hydrocarbons passed 255 to the methanol and olefins to gasoline conversion unit 256. A bottom fraction is withdrawn from separator 254 through conduit 257 which contains methyl tertiary alkyl etherates, such as MTBE and TAME, in admixture with $C_5+$ gasoline. The gasoline separated exhibits a high motor octane value and high research octane value. Optionally, methanol and additional hydrocarbon feedstock is passed 258,259 and 260 to conversion reactor 256. Feedstock may consist of fuel gas and propylene from a fluid catalytic cracking process. In the conversion reactor, methanol and olefins are converted at elevated temperatures between 315° and 482° C. (600° and 900° F.) to gasoline 261, LPG and lighter products 262.

The process, according to the present invention, eliminates the need for methanol recovery section in the etherification process. The excess methanol rate can be adjusted during unit operation based on the methanol feed, MTG gasoline, and ether values. Not only is the design advantageous in eliminating the methanol recovery section of the etherification process, but it confers lower cost on the MTG process and makes it more attractive for refinery applications. In the present invention, the methanol handling facility is in common with the etherification facility, and the ZSM-5 reactor in the recovery sections are in common with the olefin to gasoline unit and etherification yield is increased.

To illustrate the advantages of the present invention a comparison is presented with conventional etherification, etherification combining a slight excess of methanol with the process of oxygenates and olefins conversion to gasoline and the combined process using a large excess of methanol. Table 1 shows the product distribution for the three cases based on a 55 TBD (thousand barrels per day) FCC maximum gasoline operation. Column A is conventional etherification using 2.1% excess methanol; Column B shows the results for the integration of a conventional etherification (2.1% excess methanol) with olefins to gasoline conversion; Column C shows the results for the integration of excess etherification with olefins to gasoline conversion using 33% excess methanol.

TABLE 1

| MLB/HR | HYDROCARBON FEED | A | B | C |
|---|---|---|---|---|
| $C_1$ | 11.40 | 11.40 | 11.47 | 11.47 |
| $C_2=$ | 6.80 | 6.80 | 0.46 | 0.46 |
| $C_2$ | 12.00 | 12.00 | 12.59 | 12.61 |
| $C_3=$ | 25.78 | 25.78 | 3.37 | 3.34 |
| $C_3$ | 8.97 | 8.97 | 14.96 | 15.12 |
| $iC_4$ | 18.81 | 18.81 | 28.36 | 28.58 |
| $nC_4=$ | 33.43 | 33.43 | 5.98 | 6.25 |

TABLE 1-continued

| MLB/HR | HYDROCARBON FEED | A | B | C |
|---|---|---|---|---|
| $nC_4$ | 5.91 | 5.91 | 10.07 | 10.15 |
| $iC_4^=$ | 15.89 | 1.11 | 0.12 | 0.05 |
| $nC_5^=$ | 13.53 | 13.53 | 5.39 | 5.39 |
| $iC_5$ | 10.70 | 10.70 | 10.70 | 10.70 |
| $nC_5$ | 2.79 | 2.79 | 2.79 | 2.79 |
| $iC_5^=$ | 20.03 | 7.01 | 2.79 | 2.39 |
| $C_5+$ | — | — | 49.35 | 50.62 |
| MTBE | — | 23.21 | 23.21 | 24.21 |
| TAME | — | 18.97 | 18.97 | 20.43 |
| $H_2O$ | 0.08 | — | 0.17 | 4.25 |
| TOTAL | 186.12 | 200.42 | 200.75 | 208.90 |

The results of this investigation clearly show the superior yields of MTBE, TAME and $C_4+$ hydrocarbons achieved through the process of the instant invention. When the process of the invention is compared to alkylation to produce gasoline of comparable octane value based on the same feedstock as in Table 1, a 26% higher yield of $C_4+$ liquid product is realized with the instant invention. Also, the approximate investment cost for a 55 TBD plant is 20MM dollars for the present invention versus 35MM dollars for alkylation.

While the invention has been described by specific examples and embodiments, there is no intent to limit the inventive concept except as set forth in the following claims.

What is claimed is:

1. An integrated once through process for the production of ether-rich liquid fuels, comprising;
   (a) reacting a fresh mixture of excess methanol in a hydrocarbon feedstock containing $C_4+$ isoalkenes in the presence of acidic etherification catalyst under etherification conditions whereby an etherification effluent stream containing methyl tertiary alkyl ethers is produced;
   (b) separating said etherification effluent stream to provide a first stream comprising ether-rich gasoline and a second stream comprising unreacted methanol and olefinic hydrocarbons; and
   (c) contacting said second stream with an acidic metallosilicate catalyst under olefinic and oxygenates conversion conditions at elevated temperature whereby $C_6+$ gasoline is produced.

2. The process of claim 1 comprising the further step of mixing step (b) second stream with an auxiliary feedstock comprising $C_2$–$C_5$ alkenes before contacting with the acid metallosilicate catalyst in step (c).

3. The process of claim 1 wherein said step (b) second stream comprises an azeotropic mixture of lower alkyl alcohol and olefinic hydrocarbons and said first stream comprises $C_5+$ ether-rich gasoline.

4. The process of claim 2 wherein said $C_2$–$C_5$ alkene auxiliary feedstock and step (a) hydrocarbon feedstock contain light inert components whereby the exothermic temperature rise of step (c) conversion conditions is diluted.

5. The process of claim 1 wherein the etherification conditions comprise up to 100% stoichiometric excess of said methanol over $C_4+$ isoalkenes whereby the etherification reaction equilibrium is shifted substantially toward the formation of $C_5+$ ethers.

6. The process of claim 5 wherein said stoichiometric excess of lower alkyl alcohol is about 50 percent.

7. The process of claim 1 wherein said methyl tertiary alkyl ethers comprise MTBE and TAME.

8. The process of claim 1 wherein said metallosilicate catalyst comprises a crystalline, medium pore, acid aluminosilicate zeolite-type catalyst.

9. The process of claim 1 wherein step (b) first stream comprises $C_5+$ ether-rich gasoline having high motor octane and research octane values.

10. An integrated continuous process for producing tertiary alkyl ethers and gasoline range hydrocarbons comprising the steps of:
    (a) contacting a first liquid reaction mixture in a single pass with an acid etherification catalyst under etherification conditions, said first reaction mixture comprising $C_4$–$C_9$ hydrocarbons containing $C_4$–$C_7$ isoalkene components and $C_6+$ gasoline range non-etherifiable aliphatic components, and a lower alkyl alcohol reactant, said alcohol being present in more than 30% stoichiometric excess of the isoalkene component;
    (b) recovering an etherification reaction effluent containing $C_5+$ tertiary alkyl ether, gasoline range hydrocarbons, unreacted alcohol and light olefinic hydrocarbons;
    (c) distilling the etherification reaction effluent to provide a first product stream comprising a liquid mixture of $C_5+$ ether and gasoline range hydrocarbons, and a second volatile low molecular weight reaction mixture comprising unreacted alcohol and light olefinic hydrocarbons; and
    (d) contacting the second reaction mixture with an acid medium pore metallosilicate zeolite catalyst at elevated temperature to convert the alcohol and light olefinic hydrocarbons to a second product stream having average molecular weight greater than the second reaction mixture.

11. The process of claim 10 wherein the first reaction mixture consists essentially of a mixture of butenes rich in iso-olefins, light olefinic naptha and methanol, and methanol being present in at least ⅓ stoichiometric excess of the isoalkene components; wherein the second reaction mixture comprises unreacted methanol and butylenes; and wherein the zeolite catalyst comprises aluminosilicate having the structure of ZSM-5.

12. The process of claim 11 wherein the second reaction mixture is supplemented with an added $C_2$–$C_5$ olefin stream.

13. The process of claim 11 wherein the first product stream comprises MTBE, TAME and unreacted naphtha.

14. An integrated, once through reactor system for iso-olefin etherification to MTBE and TAME and conversion of oxygenates and olefins to gasoline, comprising in combination:
    first reactor means for containing etherification catalyst under etherification conditions;
    first fluid handling means for passing lower alkyl alcohol to said first reactor means;
    second fluid handling means for passing $C_4+$ hydrocarbons to said first reactor means;
    separator means operatively connected to said first reactor means for separating effluent therefrom;
    second reactor means for conversion of oxygenates and olefins operatively connected to said separator to receive unreacted and hydrocarbon overhead vapor therefrom;
    third fluid handling means for optionally passing auxiliary feedstream to said second reactor.

* * * * *

UNITED STATES PATENT AND TRADEMARK OFFICE
CERTIFICATE OF CORRECTION

PATENT NO. : 4,826,507

DATED : May 2, 1989

INVENTOR(S) : Mohsen N. Harandi et al.

It is certified that error appears in the above-identified patent and that said Letters Patent is hereby corrected as shown below:

Col. 7, line 52, delete "Euroopean" and insert --European--.
Col. 8, line 25, after "additional" insert --olefinic light gas--.
Col. 9, line 52, delete "lower alkyl alcohol" and insert --methanol--.
Col. 9, line 65, delete "lower alkyl alcohol" and insert --methanol--.
Col. 10, line 37, delete the second occurrence of "and" and insert --said--.
Col. 10, line 56, delete "lower alkyl alcohol" and insert --methanol--.
Col. 10, Claim 14, line 63, after "unreacted" insert --methanol--.

Signed and Sealed this

Twentieth Day of March, 1990

Attest:

JEFFREY M. SAMUELS

*Attesting Officer*  *Acting Commissioner of Patents and Trademarks*